(12) United States Patent
Heller (10) Patent No.: US 7,841,997 B1
(45) Date of Patent: Nov. 30, 2010

(54) SLING WITH POCKETS

(76) Inventor: Tracy Heller, 102-30 66th Rd., Forest Hills, NY (US) 11375

( * ) Notice: Subject to any disclaimer, the term of this patent is extended or adjusted under 35 U.S.C. 154(b) by 0 days.

(21) Appl. No.: 11/788,971

(22) Filed: Apr. 23, 2007

(51) Int. Cl.
*A61F 5/00* (2006.01)
*A61F 5/40* (2006.01)

(52) U.S. Cl. ............................................ 602/4; 128/878

(58) Field of Classification Search ............ 602/4; 128/869, 874, 878; 150/104, 107, 109, 112, 150/113, 117, 118
See application file for complete search history.

(56) References Cited

U.S. PATENT DOCUMENTS

| | | | |
|---|---|---|---|
| 114,615 A | | 5/1871 | Smitley |
| 2,088,927 A | * | 8/1937 | Roy ................................ 602/4 |
| 2,306,715 A | | 12/1942 | Rubinstein |
| 2,560,243 A | | 7/1951 | Peterson |
| 3,189,073 A | * | 6/1965 | Todd ........................... 224/222 |
| 3,307,538 A | | 3/1967 | Groll |
| 4,263,951 A | * | 4/1981 | Siegel ........................... 150/111 |
| 4,285,337 A | * | 8/1981 | Cosentino ........................ 602/4 |
| 4,510,928 A | | 4/1985 | Ackley |
| 4,526,164 A | | 7/1985 | Bihl |
| 4,625,719 A | * | 12/1986 | Chambers ........................ 602/4 |
| 4,759,353 A | * | 7/1988 | Melendez et al. ............... 602/4 |
| 4,878,490 A | | 11/1989 | Scott |
| 4,901,713 A | | 2/1990 | Troeger |
| 5,086,762 A | | 2/1992 | Chee |
| 5,141,488 A | | 8/1992 | Schrader |
| 5,290,218 A | | 3/1994 | Kilbey |
| 5,334,132 A | * | 8/1994 | Burkhead ........................ 602/4 |
| 5,358,470 A | | 10/1994 | Johnson |
| 6,030,354 A | | 2/2000 | Lakusiewicz |
| 6,099,489 A | | 8/2000 | Herzberg et al. |
| 6,190,340 B1 | | 2/2001 | Borell |
| 6,406,449 B1 | | 6/2002 | Moore et al. |
| 6,435,185 B1 | | 8/2002 | Schimpl |
| 6,453,904 B1 | | 9/2002 | Wilson et al. |
| 6,595,936 B1 | | 7/2003 | Oladipo |
| 6,918,885 B2 | * | 7/2005 | Moore et al. ................... 602/4 |
| 6,974,428 B2 | | 12/2005 | Knutson et al. |

(Continued)

OTHER PUBLICATIONS

Super Sling-Universal Shoulder Immobilizer, SupportsUSA, at least as early as May 9, 2006 (http://www.supportsusa.com/arm/shoulder2/supersling.htm).

(Continued)

*Primary Examiner*—Patricia M Bianco
*Assistant Examiner*—Keri J Nicholson
(74) *Attorney, Agent, or Firm*—Brandon N. Sklar, Esq.; Kaye Scholer LLP (57) ABSTRACT

Embodiments of the invention relate to a sling having pockets positioned such that an individual wearing the sling may access them. In one embodiment of the invention, the sling may include a strap configured to be worn over a shoulder of an individual and a U-shaped support member depending from the strap. The U-shaped support member may form a channel configured to support an arm of the individual. The sling may also include at least one pocket positioned internal to the U-shaped support member such that the at least one pocket may be accessible to the individual. In another embodiment of the invention, the sling may include two straps for supporting the support member and an individual's arm.

18 Claims, 10 Drawing Sheets

U.S. PATENT DOCUMENTS

| | | | |
|---|---|---|---|
| 6,974,429 | B2 | 12/2005 | Moore et al. |
| 6,979,303 | B2* | 12/2005 | Jestrabek-Hart ............... 602/4 |
| 7,037,281 | B1 | 5/2006 | Jeffrey et al. |
| 2002/0082537 | A1* | 6/2002 | MacAllister .................. 602/4 |
| 2002/0156406 | A1 | 10/2002 | Moore et al. |
| 2002/0156407 | A1 | 10/2002 | Estep |
| 2005/0015033 | A1 | 1/2005 | Moore et al. |
| 2005/0273026 | A1* | 12/2005 | Howard ....................... 602/20 |
| 2006/0189906 | A1* | 8/2006 | Nelin et al. .................... 602/4 |

OTHER PUBLICATIONS

The Ultimate Arm Sling, The Joslin Swathe, Joslin Orthopedic Gear, 2006 (http://www.armsling.com).

Breg Shoulder Stabilizer, SupportsUSA, 2006 (http://www.supportsusa.com/arm/breg/shoulder/shoulder-stabilizer.htm).

Anatomy of a Handbag, Yolanda Wikiel, Style Magazine p. 143; Oct. 2006.

* cited by examiner

Figure 9

SLING WITH POCKETS

FIELD OF THE INVENTION

Embodiments of the invention relate to slings and, more particularly, to a sling with pockets.

BACKGROUND OF THE INVENTION

The medical and physical therapy fields have employed slings for years in order to stabilize an arm and provide rest after an arm injury. Patients with arm injuries or paralysis often find comfort by supporting the injured arm with a traditional sling. A traditional sling includes a fabric support member formed as a longitudinal channel with one open end and a closed end for receiving the elbow of the user. Traditionally, the forearm extends along the length of the longitudinal channel with the user's hand positioned adjacent to the open end. A strap traditionally connects the open and closed ends of the sling and extends over one shoulder and across the back of a patient when worn.

After serious arm injuries, the arm may need to be immobilized as much as possible. Often, the sling securely holds the elbow in the longitudinal channel, such that the arm does not accidentally slip out of the sling. In some cases, a strap connected to the sling wraps around the body of the user and secures the injured arm against the body. Although such an arrangement provides immobilization and support in some cases, the sling and the injured arm make some pants and/or shirt pockets impossible to use.

SUMMARY OF THE INVENTION

A patient with an injured arm supported in a sling may have diminished access to their clothing pockets, wallets, purses, pocket books, and useful storage. For example, patients with injured right hands may have significant difficulty accessing right hand pants pockets. As such, patients may have few usable pockets available for use while recovering from an injury.

One embodiment of the invention includes a sling to be worn by an individual. The sling may include a suspension structure configured to be worn over at least one shoulder of an individual and a U-shaped support member depending from the first strap and forming a channel configured to support an arm of the individual. The U-shaped support member may have a first surface positioned internal to the channel. The sling may also include a pocket positioned on the first, internal surface of the U-shaped support member and configured to be accessible to the individual.

Another embodiment of the invention includes a sling to be worn by an individual for supporting an arm. The sling may include a first strap having a first end and a second end, a second strap having a third end and a fourth end, and a U-shaped support member forming a channel and configured to support an arm of an individual. The support member may include a first portion coupled to the first end of the first strap and the third end of the second strap and a second portion coupled to the second end of the first strap and the fourth end of the second strap. The support member may also include a first surface of the support member positioned internal to the channel. The sling may also include at least one pocket positioned on the first surface of the support member and internal to the open channel and configured to be accessed by the individual.

DETAILED DESCRIPTION OF THE INVENTION

The present disclosure will now be described more fully with reference to the Figures in which various embodiments of the invention are shown. The subject matter of this disclosure may, however, be embodied in many different forms and should not be construed as being limited to the embodiments set forth herein.

Embodiments of the invention relate to a sling having at least one pocket, or other such compartment to contain items, arranged on a support member configured to support an individual's arm in the event of an injury to the arm, shoulder, hand, or any other body part where it is beneficial to support or immobilize an arm. The one or more pockets may be placed on the inside of the sling's support member in order to provide easily accessed and secure storage space when wearing a sling. In one example of an embodiment of the invention, a sling may be constructed having two straps, a support member, and at least one pocket or compartment arranged on the support member such that an individual wearing the sling may place either arm in the support member and have increased personal storage available to the other arm via the at least one pocket or compartment.

Figure 1:
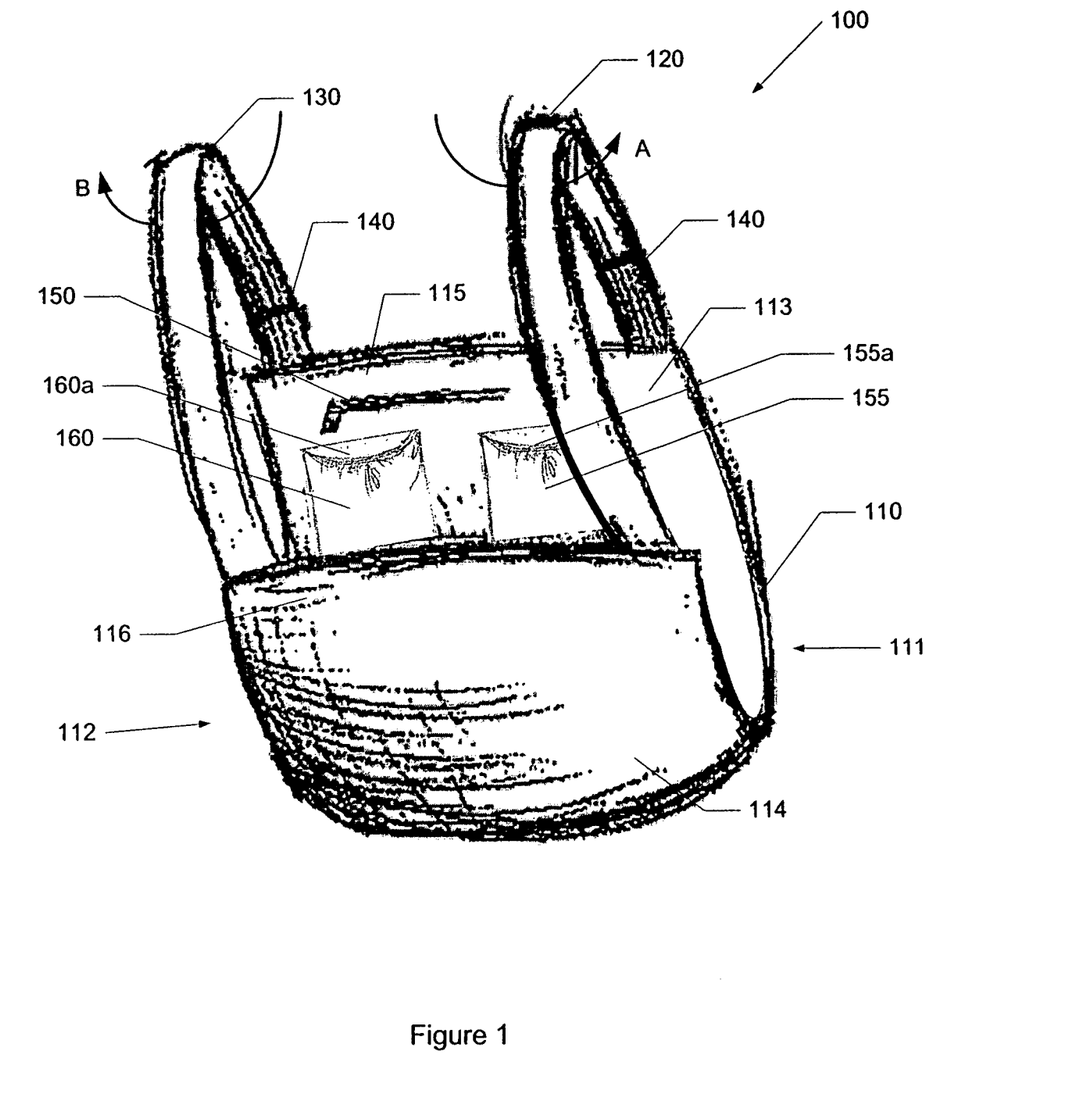
FIG. 1 shows a perspective view of an example of a sling with pockets from the front in accordance with an embodiment of the invention.
Figure 2:
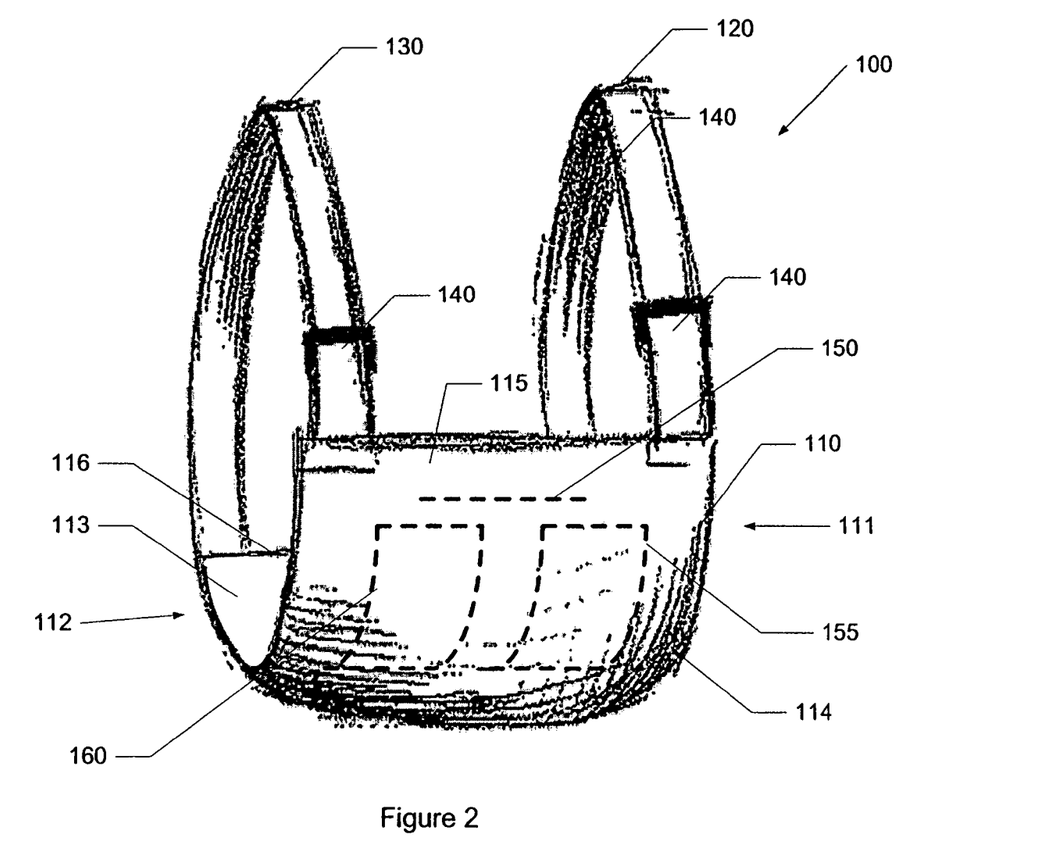
FIG. 2 shows a perspective view of the sling of FIG. 1 from the rear in accordance with an embodiment of the invention.

FIGS. 1 and 2 show an example of a sling 100 from the front and from the back, respectively. In accordance with an embodiment of the invention, the sling 100 includes a support member 110, a strap 120, and a strap 130. As shown, the support member also includes a first open end 111 and a second open end 112. As shown in FIG. 1, the support member 110 may be positioned to form a longitudinal cradle or channel structure having a first interior surface 113 and a second exterior surface 114. When folded or shaped into the cradle or channel structure, the support member forms a first half 115 to be positioned against an individual's chest or stomach and a second half 116 opposite the first half, allowing a patient to rest an injured arm between the two halves. Each of the straps 120 and 130 may include an adjustment apparatus 140, such as buckles, D-rings, VELCRO® or other such adjustment means, for adjusting the length of the straps 120 and 130. FIG. 1 also shows a zipper pocket 150 and pockets 155 and 160 formed in the surface of the first surface 113. Additional pockets, for example, may be formed or placed on the second surface 114. As used herein, the term pocket is intended to include a pockets formed on a surface, such as pockets 155 and 160, for example, and pockets formed in a surface or lining, such as the zipper pocket 150.

Figure 3:
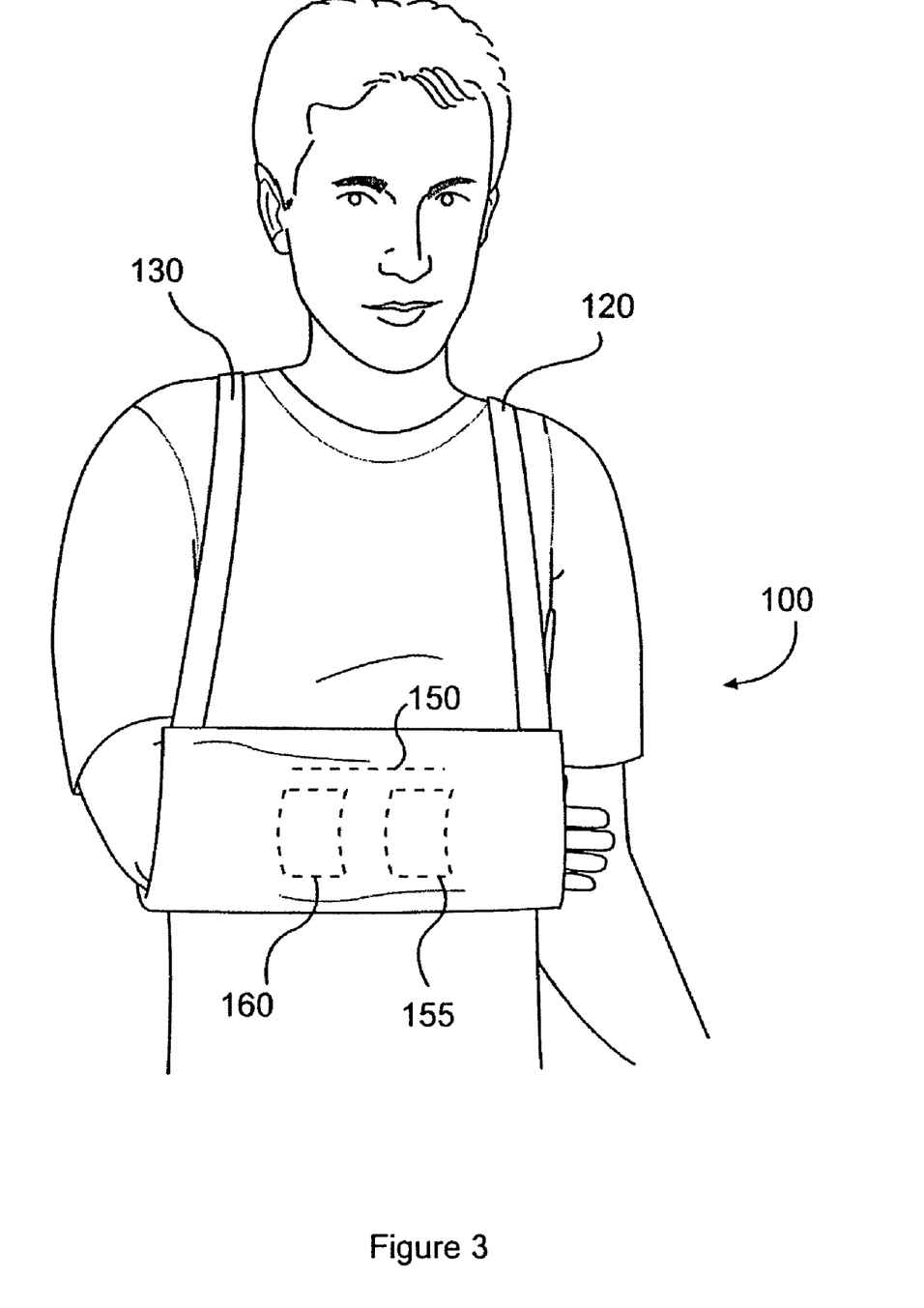
FIG. 3 shows a perspective view of an individual wearing an example of the sling shown in FIGS. 1 and 2 in accordance with an embodiment of the invention.

A patient may wear the sling 100 by placing both straps on their shoulders, as shown in FIG. 3. Specifically, the patient may wear the sling 100 by placing the strap 120 on their left shoulder while placing their left arm through the strap 120 (as indicated by the arrow A in FIG. 1). Likewise, a patient may place the strap 130 on their right shoulder by placing their right arm through the strap 130 (as indicated by the arrow B in FIG. 1). Once the straps 120 and 130 are properly adjusted for length, the support member 110 provides a cradle with part of the second surface 114 of the first half 115 resting against the patient's chest and/or stomach. A right arm may be supported by placing the right arm through the open end 112 and allowing the forearm of the right arm to rest on the first surface 113 between the first half 115 and a second half 116 of the support member 110, as shown in FIG. 3. Depending on the length of the arm and the width of the support member from one end to the other; the right hand may extend beyond the open end 111. Similarly, a left arm may be supported by placing the left arm through the open end 111 and allowing the forearm of the left arm to rest on the first surface 113 between the first half 115 and a second half 116 of the support member 110. Depending on the length of the arm and the width of the support member from one end to the other, the left hand may extend beyond the open end 112. The sling 100, including the straps, support member, and pockets, may be fabricated from fabric or other suitable materials known to those of skill in the art.

Figure 8:
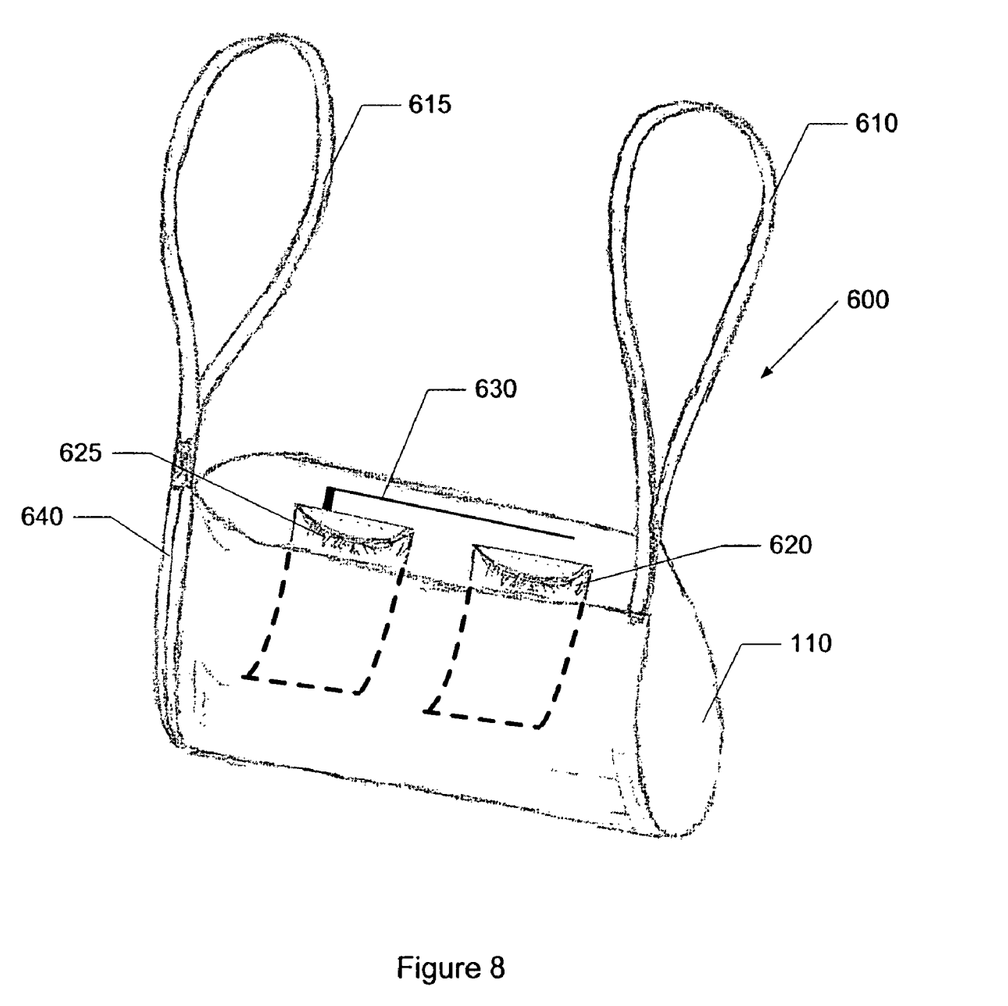
FIG. 8 shows a perspective view of an example of another sling with a pocket arrangement in accordance with an embodiment of the invention.

The arrangement of the sling 100 may allow easy removal of an injured arm from the sling by simply pulling the arm longitudinally out of the support member 110. Alternatively, it is also contemplated that the support member 110 may be closed at one end to provide additional support for an elbow as shown in FIG. 8 and discussed below.

The sling 100 may provide a patient with one or more pockets 150, 155, and 160 for storing personal items. In particular, a patient may use the pockets 150, 155, and 160 to store items that would typically be handled by their injured arm and stored in the pockets that may be difficult to access by the injured arm. The good arm can access the pockets 150, 155, 160 instead. For example, if a right arm is injured and placed in the sling 100, the patient may use pockets 150, 155, and 160 to hold items, such as a wallet, keys, cell phone, blackberry and other personal items, which normally fit within the patient's right hand pants or shirt pockets and/or clipped to the right hand side of an individual's belt, shirt or pants.

It is also contemplated that the pockets 155 and 160 may be alternatively arranged longitudinally such that the pocket opening 155a of the pocket 155 faces toward the open end 111 and the pocket opening 160a of the pocket 160 faces toward the open end 112. Such a longitudinal arrangement of the pocket 155 may provide access directly from the side for the left hand. Likewise, the pocket 160 may provide access directly from the side for the right hand. Such a configuration is shown in FIG. 4A.

As an example, embodiments of the invention allow a patient to store sensitive personal items, such as wallets and identification, on the inside of the longitudinal channel formed by the support member 110 of the sling 300. By placing pockets on the inside of the longitudinal channel formed by the support member 110, items stored in the pockets of the sling may be less accessible to strangers or less vulnerable to incidental contact with others when in a crowd. Without the pockets 150, 155, and 160, as shown in FIG. 1, a patient would have significantly reduced pocket or storage space when wearing the sling 100. It should be understood that the placement, number and size of the pockets shown in FIG. 1 may be changed and reconfigured without deviating from the spirit and scope of the invention.

FIG. 3 shows a perspective view of an individual wearing an example of the sling 100 shown in FIGS. 1 and 2. As shown, the sling includes pockets 155 and 160 and a zippered pocket 150 depicted in dashed lines. As with the sling shown in FIGS. 1 and 2, the pockets 150, 155, and 160 may be positioned on the internal surface of the sling and on the first half of the sling resting up against the individuals chest and/or stomach. The sling 100 may be configured to have a sufficient length in order to support both the elbow and the hand of the individual. For example, the sling 100 shown in FIG. 3 extends from under the individual's right elbow to under the individual's right hand, potentially providing support to the individual's right hand, right arm, and/or even the individual's right shoulder and neck.

Figure 4:
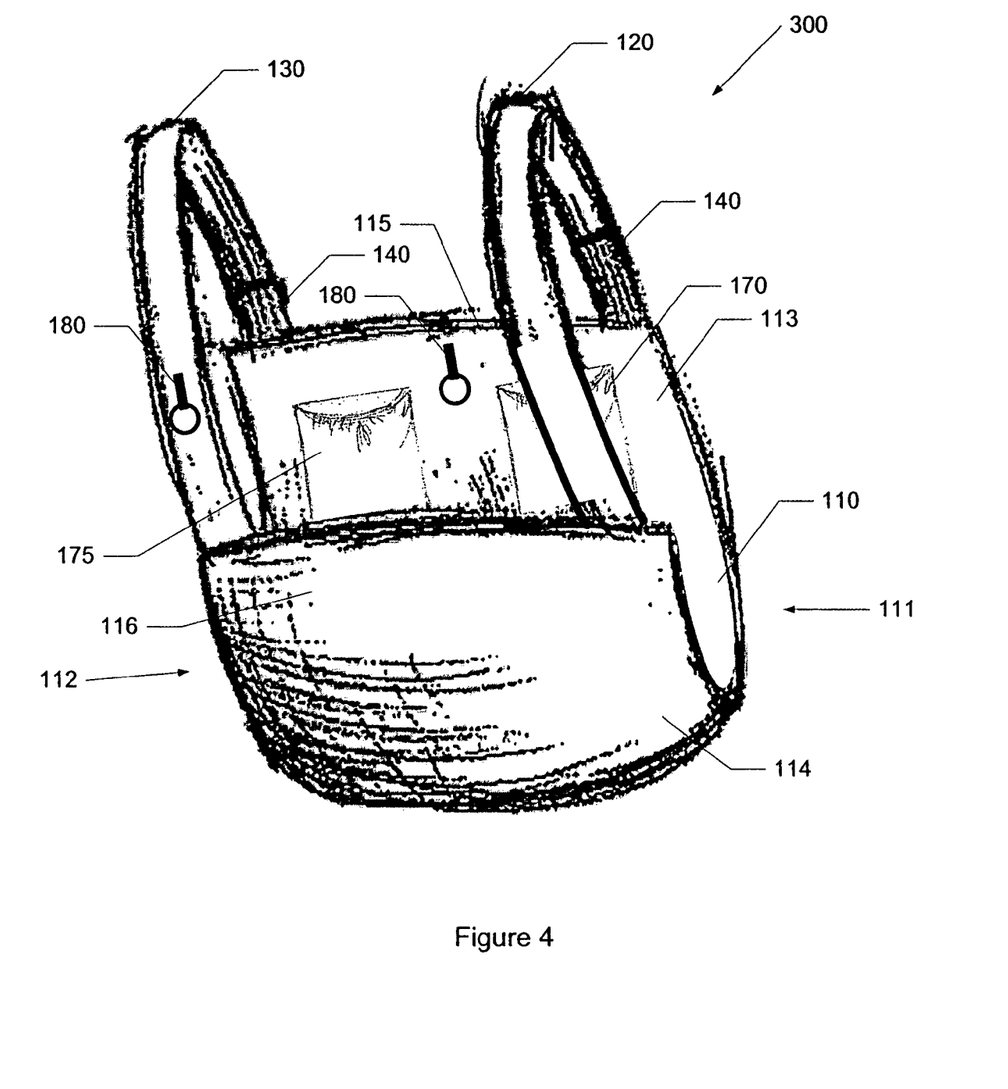
FIG. 4 shows a perspective view of an example of another sling with a pocket arrangement in accordance with an embodiment of the invention.
Figure 4A:
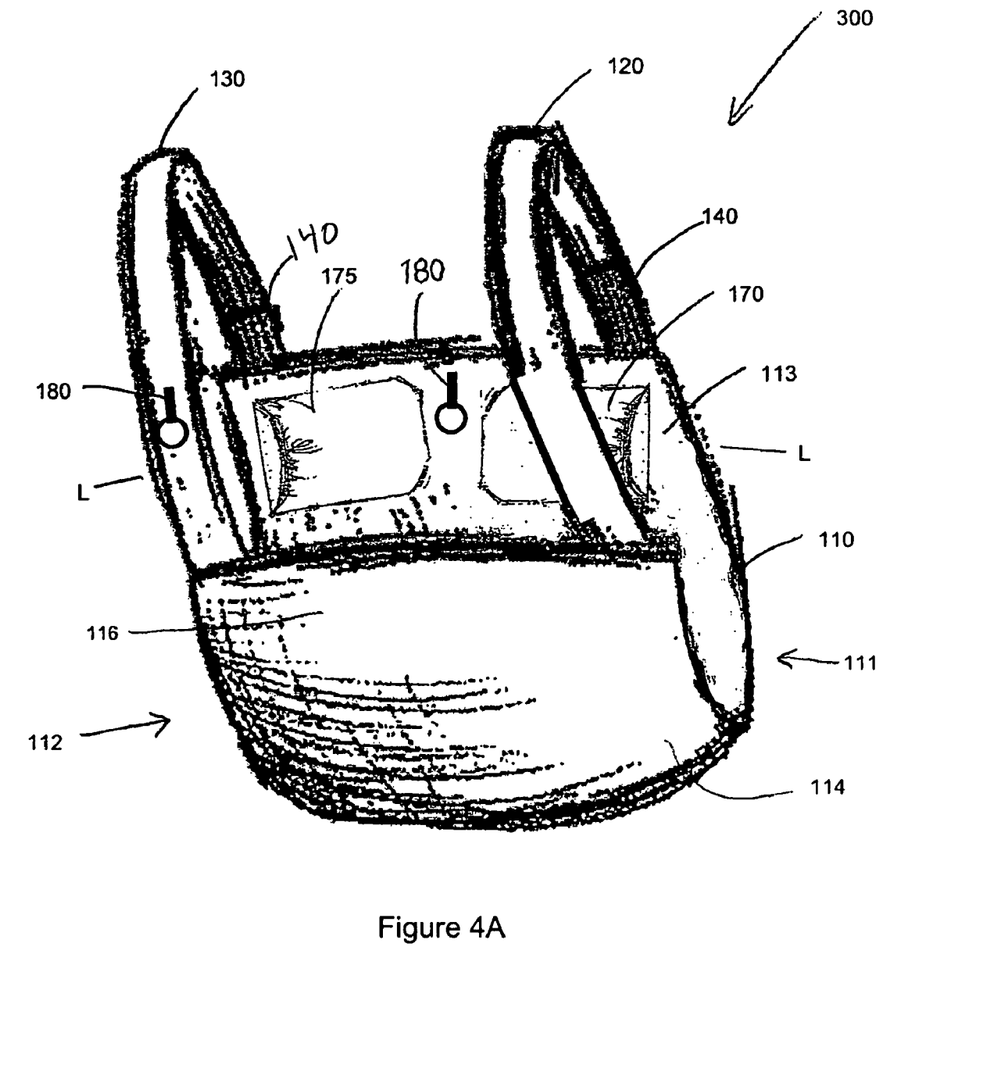
FIG. 4A shows a perspective view of another example of the sling of FIG. 4.

FIG. 4 illustrates an alternative embodiment of a sling 300 having pockets 170 and 175 mounted on the first surface 113 and a clip 180, which may act as a key ring holder, for example. As with the pockets 155 and 160, the pockets 170 and 175 may be arranged longitudinally along a longitudinal axis L of the support member 110 such that a patient may easily access the pockets from the side, as shown in FIG. 4A.

The clip 180 may aid a patient by increasing the usable pocket space or personal storage when wearing the sling 300. The clip 180 may be configured to retain a set of keys or other items that may be clipped to the sling 300 for easy and quick access. It should be understood that one or more clips 180 may be positioned on the sling 300. For example, as shown in FIG. 4, the clips 180 may be positioned on various locations on the sling 300, including on the strap 130 and the first surface 113. By placing the clip 180 on the first surface 113 and inside the sling 300, the clip 180 may be securely held close to the body of the patient and away from casual contact with strangers or thieves. Additionally, the sling 300 may include a clip 180 placed at one or both of the open ends 111 and 112 of the sling 300 such that the clip may be easily accessed by a patient's hand. Likewise, the placement of the clip 180 may be changed and placed anywhere on the first surface 113, the second surface 114, or on the straps 120 and 130. While in this discussion the clip 180 includes holding items such as sets of keys, other items may be attached to the clip 180 and the clip 180 may represent other types of connectors or storage devices.

Figure 5:
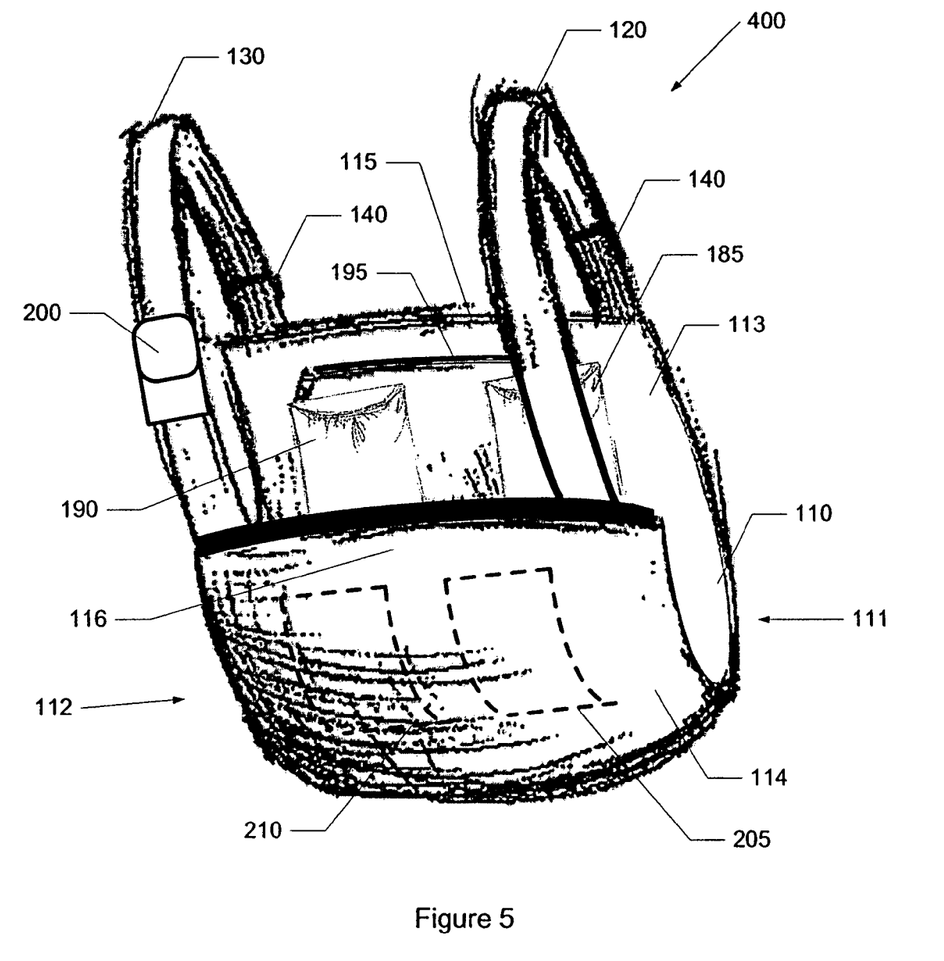
FIG. 5 shows a perspective view of another example of a sling with a different pocket arrangement in accordance with an embodiment of the invention.

FIG. 5 shows an alternative sling 400 that may include two sets of pockets positioned on opposing internal sides of the support member 110. The sling 400 may include two upright pockets 185 and 190 positioned on the first surface 113 and on the first half 115 of the support member 110. The sling 400 may also include a zipper pocket 195, as shown in FIG. 5. These pockets 185, 190, and 195 may be configured to provide large amounts of pocket space or storage space without increasing the overall size of the sling 100. FIG. 5 also shows (in phantom lines) two additional optional pockets 205 and 210, which are on an inner surface of the sling facing the pockets 185, 190, 195.

As an additional option, a pocket 200 may be removably attached to the strap 130. The pocket 200 may be configured to hold a cell phone, a portable music player, or other personal device. Although the pocket 200 may be secured to the strap 130, the pocket 200 may be removable and placed on the strap 120 or at other locations along the straps 120 and 130. It is contemplated that the removable pocket 200 may be attached to the strap 130 using a hook and loop fastener, such as VELCRO®, or a zipper, for example.

Figure 6:
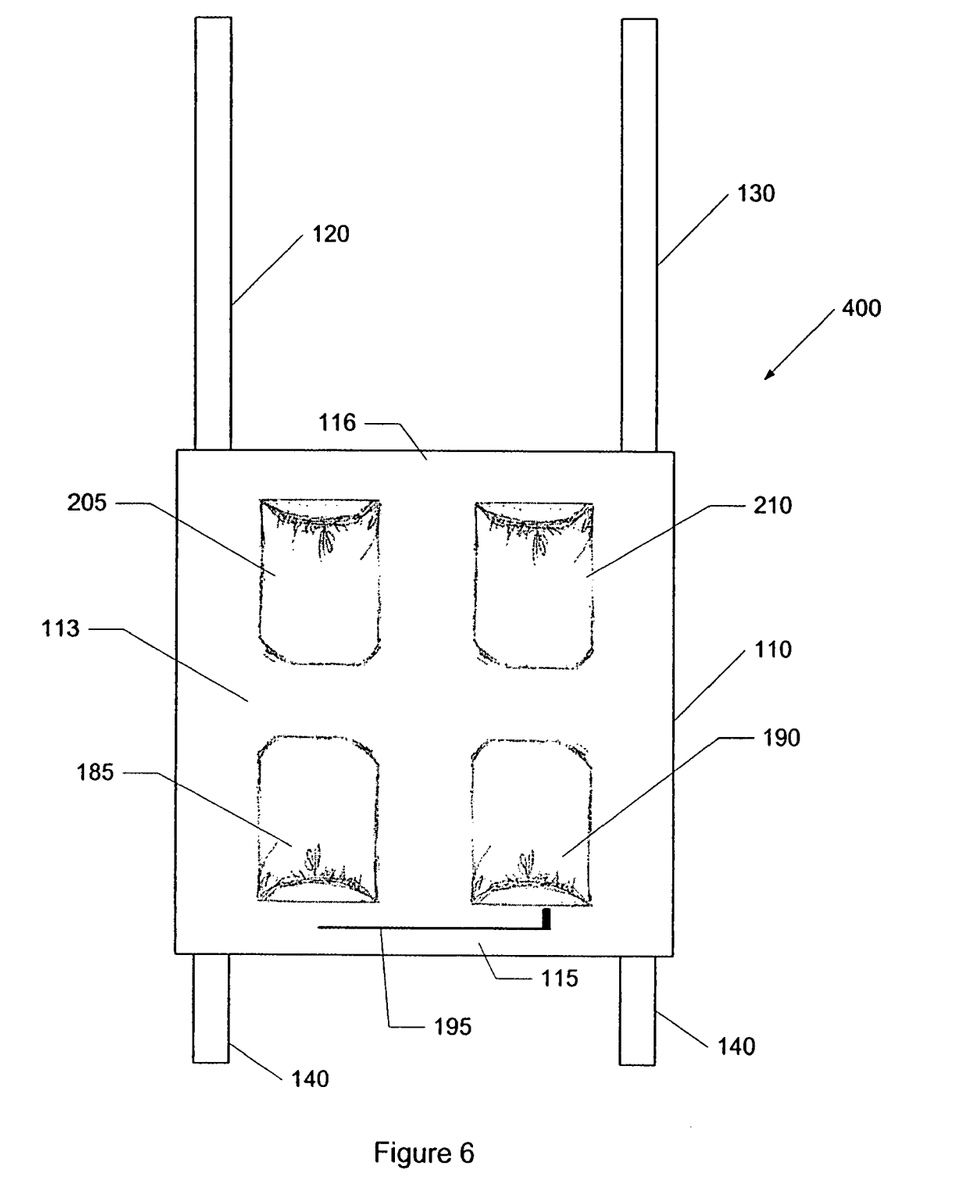
FIG. 6 shows a plan view of an example of a sling with a pocket arrangement in accordance with an embodiment of the invention.

FIG. 6 shows the sling 400 prior to connecting the straps 120 and 130 and forming the longitudinal channel from the support member 110. As shown in FIG. 6, the first surface 113 is facing upward with pockets 185, 190 and 195 positioned on the first half 115 of the support member 110. On the second half 116 of the support member 110, the sling 400 may include additional pockets 205 and 210. Alternative orientations and arrangements of the pockets shown in FIG. 6 may be used. Because the pockets 205 and 210 are positioned on the first surface 113 and on the second half 116, the pockets 205 and 210 are positioned internal to the longitudinal channel of the sling 400 and consequently are shown in phantom FIG. 5.

Referring back to FIG. 5, the arrangement of pockets 185, 190, and 195 and the pockets 205 and 210 (shown in phantom) are positioned internal to the longitudinal channel formed from the support member 110. However, should a patient wearing the sling 400 find that the pockets and their contents are impinging on the space available for the forearm in the longitudinal channel, the sling 400 may be reversed such that the pockets 185, 190, 195, 205, and 210 are positioned on the outside and the second surface 114 is internal to the longitudinal channel. Upon reversing the sling 400, the pockets 185, 190, 195, 205, and 210 may still be used as described above with respect to the various embodiments of the invention. With respect to FIGS. 5 and 6 and the sling 400, the position, number, and size of the pockets may be changed or reconfigured without deviating from the scope and spirit of the invention. Additionally, pockets may be placed on both first and second surfaces 113 and 114 and arranged at angles.

It should be understood that, in accordance with the embodiments of the invention, the first half 115 of the support member may be worn against the chest and/or stomach of a patient regardless of how the sling is assembled, as discussed with respect to FIG. 1 and sling 100. The sling may also be worn such that the second half of the support arrangement rests against the chest and/or stomach of the patient without making any change to the sling. It should also be understood that slings in accordance with embodiments of the invention may be configured such that the pockets are on the exterior surface of the sling that rests against the chest or stomach of the individual wearing the sling.

Figure 7:
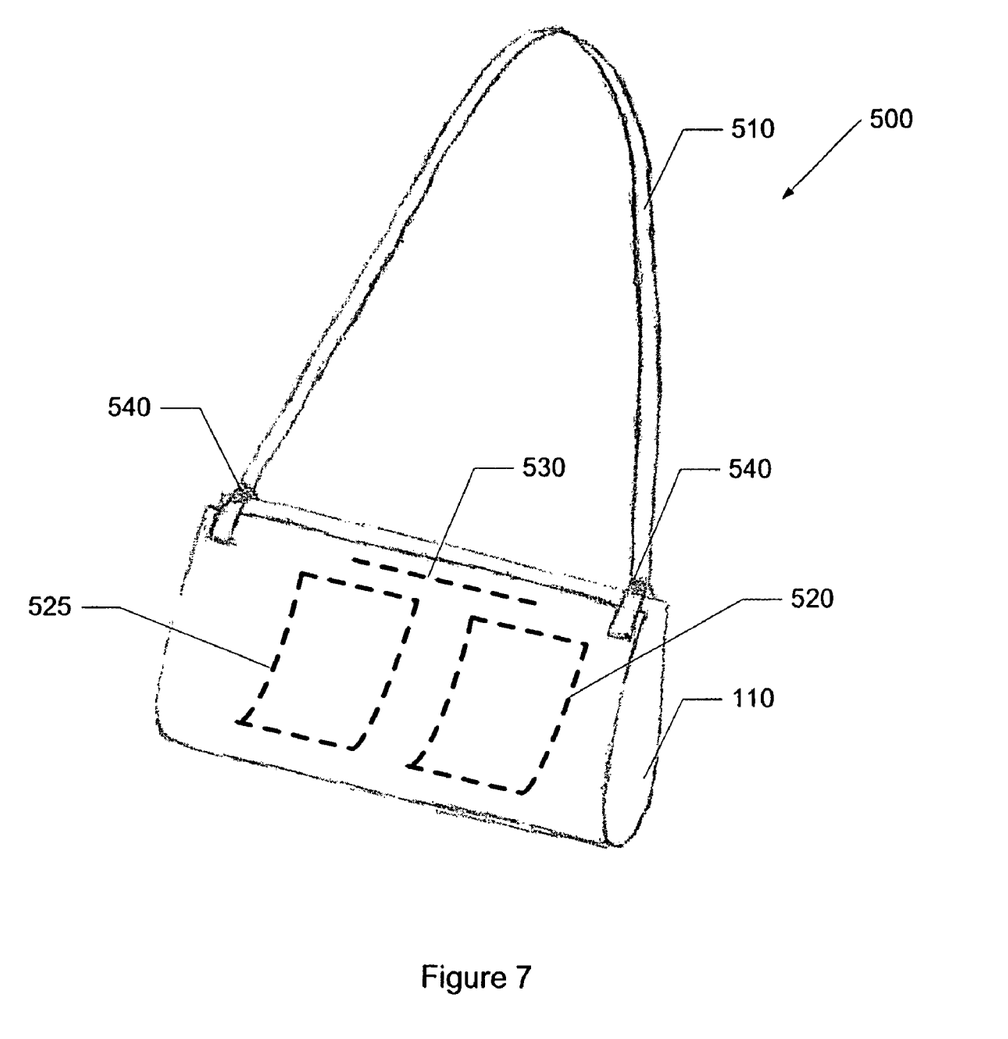
FIG. 7 shows a perspective view of an example of another sling with a pocket arrangement in accordance with an embodiment of the invention.

Additionally, an alternative embodiment of the invention may include supporting the support member 110, shown in FIGS. 1-6, using a single strap instead of two separate straps. Single strap slings are well known in the art. FIG. 7 shows an example of a sling 500 having a support member 110 and a single strap 510 connected to the support member 110 at the attachment points 540. The support member 110 may include one or more pockets 520, 525, and 530 arranged on the support member in accordance with embodiments of the invention. It should be understood that the pockets and storage devices described above and shown in FIGS. 1-6 may used and arranged on the sling 500 in the same fashion. Additionally, the strap 510 may include other strap arrangements or support structures. For example, each attachment point 540 may include two smaller straps (not shown) that depend from the strap 510 and attach to each side of the support member 110.

FIG. 8 illustrates another example of a sling 600 in accordance with an embodiment of the invention. The sling 600 may include a longitudinal channel formed from the support member 110 and supported by two straps 610 and 615. The sling 600 may also be fabricated using one strap, as shown in FIG. 7. The longitudinal channel may be closed at one end to provide elbow support and include pockets 620, 625, and 630 positioned on the inside of the support member 110. As an example, the end may be closed using a stitching 640. The end of the channel may also be closed using other means, such as, for example, hook-and-loop fasteners, buttons and/or zippers.

The openings to the pockets 155, 160, 170, 175, 185, 190, 195, 205, 210, 520, 525, 530, 620, 625, and 630 may be optionally secured or held in a closed position by elastic, zippers, hook and loop fasteners (such as VELCRO®), button fasteners or the like sufficient to prevent items from inadvertently falling out of the pockets. As discussed previously, the pockets may be oriented longitudinally with the support member. Additionally, the pockets may also be angled on diagonals or other angles to position the opening so that items in the pockets are easy to access but unlikely to fall out.

Referring to FIGS. 1-8, the upper edges of the longitudinal channels formed by the support member 110 may be configured to be closable. For example, the upper edges of the support member between the attachment points 540 of the strap 510 (shown in FIG. 7) may include a VELCRO® fastener running between the points 540 in order to seal or close the upper opening of the sling. Alternative methods, such as, for example, zippers or buttons, may be used to close the upper opening of the sling such that the pockets located on the interior of the longitudinal channel may be securely closed off from the exterior.

Figure 9:
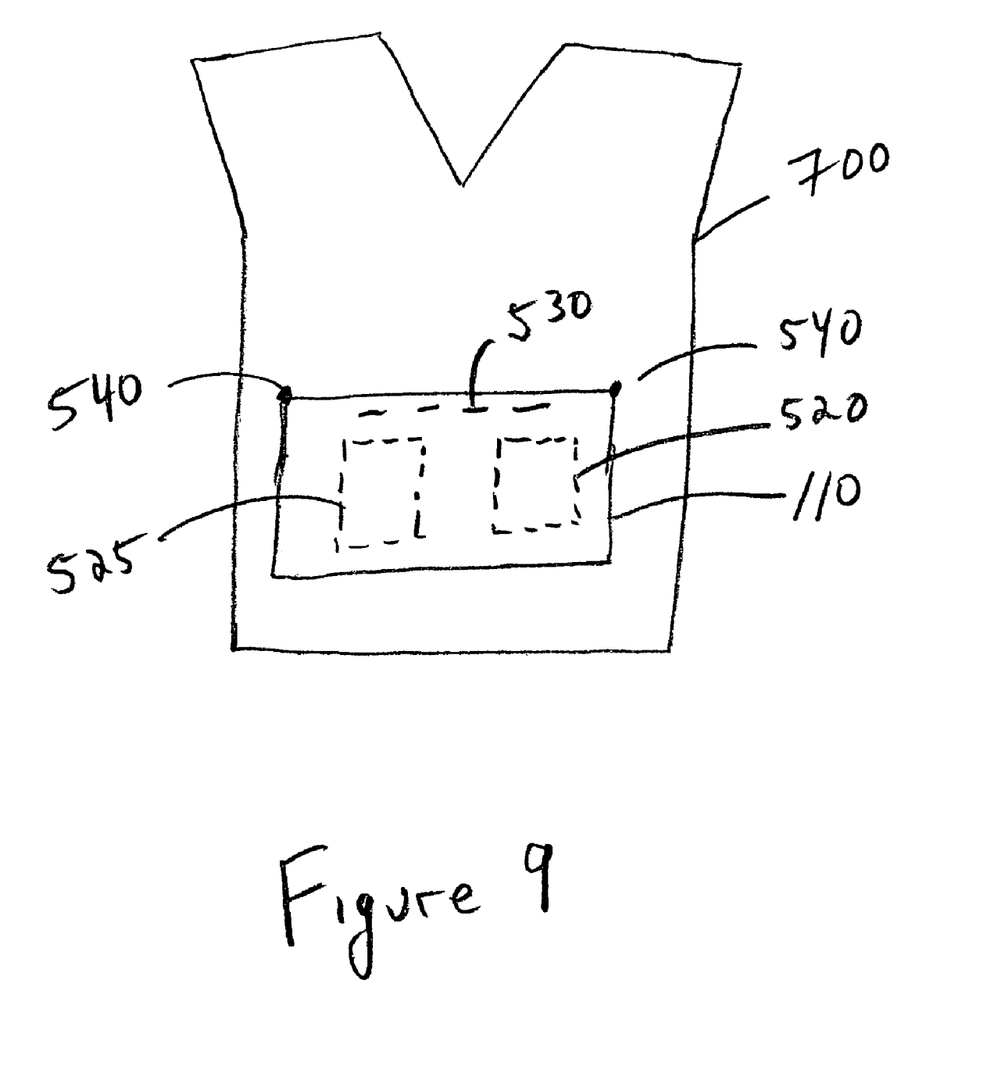
FIG. 9 is a front view of a sling supported by a vest, in accordance with an embodiment of the invention.

It should be noted that the embodiments of the invention shown in FIGS. 1-8 provide examples of a sling that is optionally universal and equally useful with either arm of a patient. Furthermore, should a patient desire to rest both arms in the sling, some embodiments may be configured to easily accommodate such an arrangement. Additionally, although the embodiments illustrated in the figures use one or more straps as the suspension structure for the support member 110, it should be understood that other forms of supporting structures may be used. For example, a vest or other garment may be used instead of straps to suspend the support member 110. In one example, the support member 110, shown in FIG. 7, may be attached to the front of a vest 700 at the attachment points 540 using D-rings or other such attachment devices to suspend the support member 110 without the use of the strap 510, as shown in FIG. 9. Additional straps or other supporting structure wrapping around the arm and/or the body may be combined with embodiments of the invention.

The foregoing descriptions of specific embodiments of the invention are presented for purposes of illustration and description. They are not intended to be exhaustive or to limit the invention to the precise forms disclosed. One skilled in the art will recognize that other changes may be made to the embodiments described herein without departing from the spirit and scope of the invention, which is defined by the claims, below.

What is claimed is:
1. A sling to be worn by an individual, the sling comprising:
 a suspension structure configured to be worn over at least one shoulder of an individual;
 a U-shaped support member depending directly from the suspension structure and forming a channel configured to support an arm of the individual, the channel having at least one open vertical side, the U-shaped support member having a first surface internal to the channel; and at least one pocket positioned on the first surface of the U-shaped support member, the at least one pocket configured to contain at least one item and to be accessible by the individual while wearing the sling;

wherein at least a first one of the at least one pockets is adjacent to a first one of the at least one open vertical sides, is substantially aligned with a longitudinal axis defined by the channel, and includes a pocket opening facing towards the first open vertical side.

2. The sling of claim 1, wherein the at least one pocket includes a zippered opening.

3. The sling of claim 1, wherein the channel formed by the U-shaped support member includes a first upper edge and a second upper edge, the first and second upper edges being configured to be releasably attachable to each other.

4. The sling of claim 3, wherein the first and second upper edges are releasably attachable to each other by at least one of a zipper, a button, or a hook and loop fastener.

5. The sling of claim 1, further comprising a clip positioned on the support member, the clip having a first portion coupled to the sling and a second portion not coupled to the spring, the second portion being configured to attach to an item not part of the sling.

6. The sling of claim 5, further comprising a removable pocket attached to the suspension structure.

7. The sling of claim 5, wherein the first portion of the clip is coupled to the first, internal surface of the U-shaped support member.

8. The sling of claim 1, wherein the suspension structure includes an adjustable strap.

9. The sling of claim 1, wherein the suspension structure includes a garment adapted to suspend the U-shaped support member.

10. The sling of claim 1, further comprising an external pocket positioned on the support member and external to the open channel such that the external pocket is adjacent to the individual's chest.

11. The sling of claim 1, wherein the suspension structure and the U-shaped support member are reversible such that the first surface and the at least one pocket are positioned external to the channel formed by the U-shaped support member in a reversed position.

12. A sling to be worn by an individual for supporting an arm, the sling comprising:

a first strap having a first end and a second end;
a second strap having a third end and a fourth end;
a U-shaped support member forming a channel having first and second oven ends and configured to support an arm of an individual, the channel including a longitudinal axis extending from the first open end of the channel to the second open end of the channel, the support member comprising:
  a first portion coupled to the first end of the first strap and the third end of the second strap;
  a second portion coupled to the second end of the first strap and the fourth end of the second strap; and
  a first surface of the support member positioned internal to the channel; and
a first pocket positioned on the first surface adjacent to the first open end and a second pocket positioned on the first surface adjacent to the second open end, internal to the channel, the first and second pockets each configured to contain at least one item;

wherein:
the first pocket is substantially aligned with the longitudinal axis and includes a first pocket opening facing towards the first open end;
the second pocket is substantially aligned with the longitudinal axis and includes a second pocket opening facing towards the second open end; and
at least one of the first pocket and the second pocket is accessible by the individual while wearing the sling.

13. The sling of claim 12, further comprising a clip positioned on the support member, the clip having a first portion coupled to the sling and a second portion not coupled to the sling, the second portion being configured to attach to an item not part of the sling.

14. The sling of claim 13, further comprising a removable pocket attached to at least one of the first strap or the second strap.

15. The sling of claim 13, wherein the first portion of the clip is coupled to the first, internal surface of the U-shaped support member.

16. The sling of claim 12, wherein the first strap and the second strap are adjustable.

17. The sling of claim 12, further comprising at least one pocket positioned on a second surface of the support member positioned external to the channel.

18. The sling of claim 12, wherein the first portion and the second portion of the U-shaped support member are releasably coupled by at least one of a zipper, a button, or a hook-and-loop fastener.

* * * * *